United States Patent [19]

Bender

[11] Patent Number: 4,612,925

[45] Date of Patent: Sep. 23, 1986

[54] SMALL ANIMAL INTRAVENOUS RESTRAINT SPLINT

[76] Inventor: William M. Bender, 11126 Balboa Blvd., Granada Hills, Calif. 91344

[21] Appl. No.: 633,645

[22] Filed: Jul. 23, 1984

[51] Int. Cl.[4] .................. A61F 13/00; A01K 29/00; A01K 15/00
[52] U.S. Cl. .................................. 128/133; 119/96; 119/126
[58] Field of Search .............. 119/96, 126, 143; 128/133, 85, 87 R, 87 A, 89 R, 90, 80 R, 77; 54/80

[56] References Cited

U.S. PATENT DOCUMENTS

| 606,481 | 6/1898 | Eidsmoe | 119/127 |
|---|---|---|---|
| 1,082,230 | 12/1913 | Nagle | 119/127 X |
| 1,867,215 | 7/1932 | Ettinger | 128/87 R |
| 2,237,252 | 4/1941 | Longfellow | 128/87 R |
| 2,655,916 | 10/1953 | Timmins | 128/87 R |
| 3,074,723 | 1/1963 | Esty | 128/133 |
| 3,256,880 | 6/1966 | Caypinar | 128/133 |
| 3,416,519 | 12/1968 | Dowers | 128/87 R |
| 3,724,453 | 4/1973 | Dixon et al. | 128/87 R |
| 4,280,490 | 7/1981 | Santy | 128/87 R X |
| 4,323,080 | 4/1982 | Melhart | 128/133 X |
| 4,349,016 | 9/1982 | Glassman et al. | 119/96 X |
| 4,424,764 | 1/1984 | Carlin | 119/96 |
| 4,502,477 | 3/1985 | Lewis | 128/133 |
| 4,505,270 | 3/1985 | Miles | 119/96 X |

FOREIGN PATENT DOCUMENTS 219175 2/1910 Fed. Rep. of Germany ...... 119/127

Primary Examiner—Robert E. Bagwill
Assistant Examiner—D. Neal Muir
Attorney, Agent, or Firm—J. L. Jones, Sr.

[57] ABSTRACT

A veterinary medical leg splint suitable for cat and dog restraint prevents an animal from flexing its elbow joint and effectively shutting off the flow of intravenous fluids. After placing an intravenous catheter in place in an animal foreleg in a cephalic vein, the cat and dog intravenous restraint splint is applied typically to the foreleg of the animal. The basic restraint is a washable, reusable, gas sterilizable longitudinal plastic restraint that can have two Velcro straps for attachment to a leg. The splint device has a one piece rigid strip having a longitudinal slit aperture adjacent the first splint terminus. The first of the two leg restraint straps is adjustably slidable in the longitudinal slit aperture, secured normal in the aperture by a restraint pin.

The second splint terminus has an adjacent paddle shaped terminal piece secured normal to the rigid strip. The second of the leg straps is secured normal to the splint adjacent to the paddle. A horizontal slot is also disposed across the splint at the first splint terminus.

5 Claims, 9 Drawing Figures

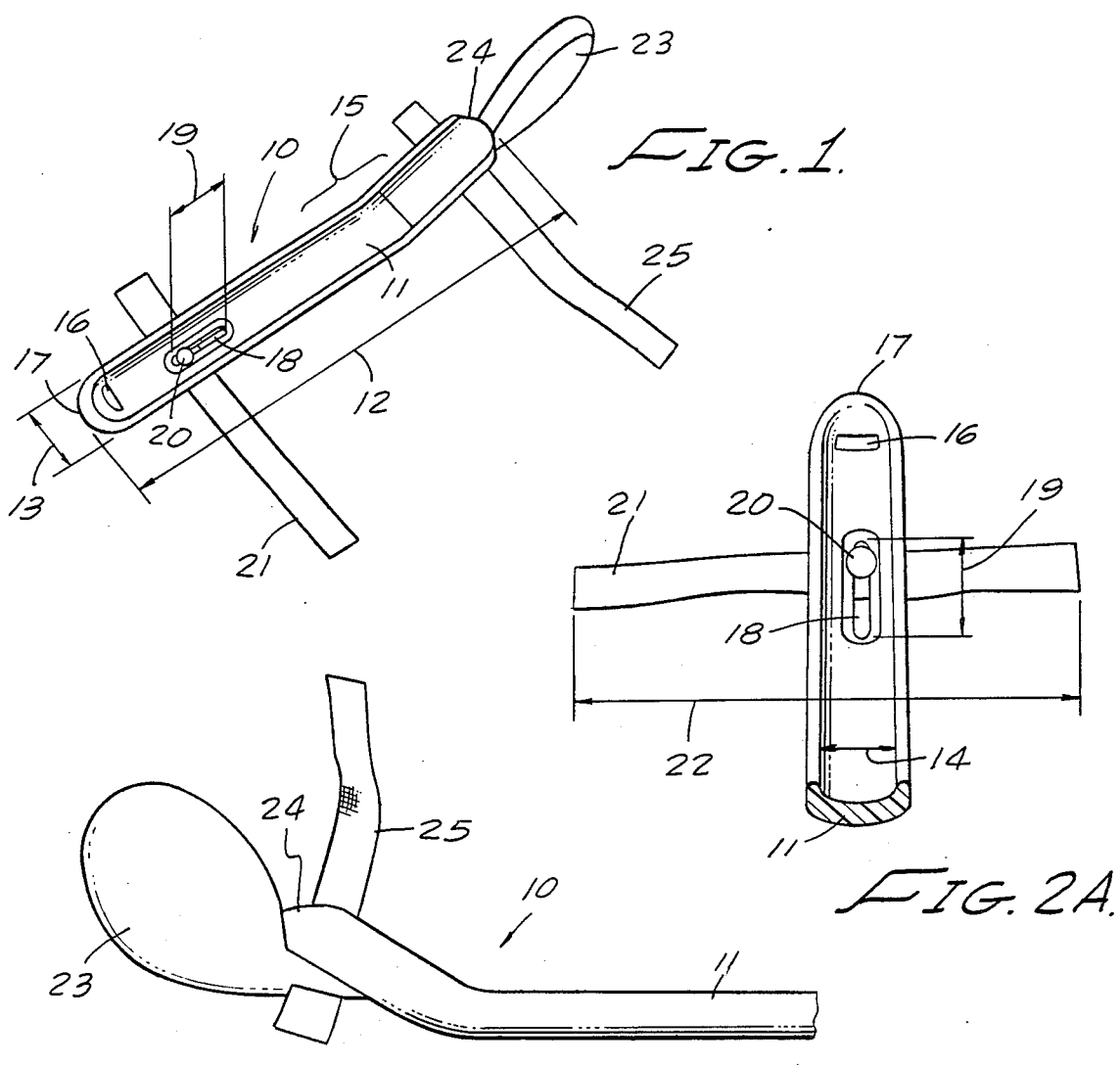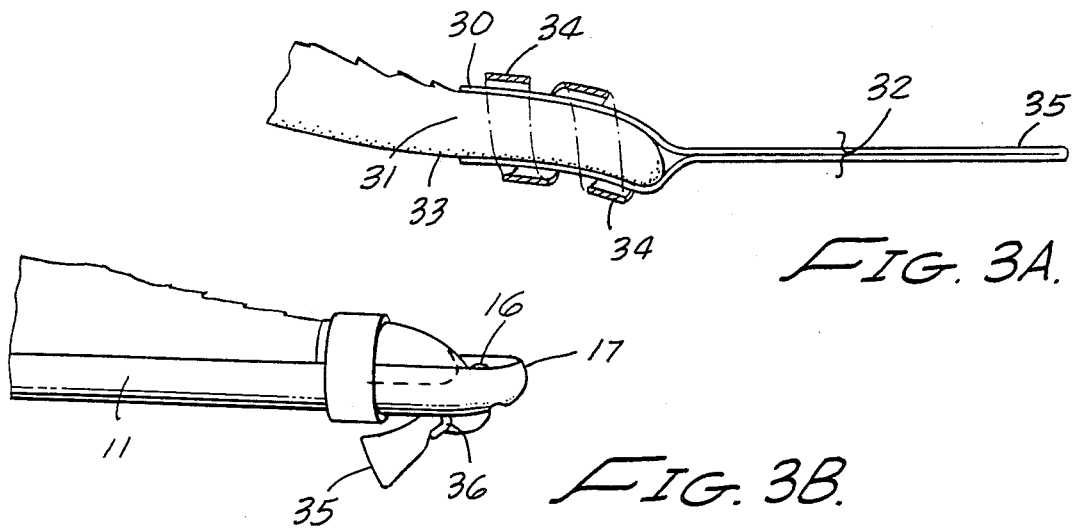

SMALL ANIMAL INTRAVENOUS RESTRAINT SPLINT

BACKGROUND OF THE INVENTION

The cat and dog intravenous restraint splint of this invention is classified in Class 119/96,96X and 127 and the like.

U.S. Pat. No. 4,505,270 issued Mar. 19, 1985 to Betty J. Miles discloses and claims an animal hospital splint for fluid administration which is disposed as a splint assembly for shielding a catheter taped to a leg. An extendable splint member is hinged to an extendable cover for accommodating a different length of leg, and a latch for securing the splint assembly to a door of a cage containing the animal receiving intravenous fluid.

U.S. Pat. No. 4,424,764 issued Jan. 10, 1984 to M. O. Carlin discloses and claims a fore leg splint or restraint for use by veterinary hospitals in the intravenous feeding of animals which immobilizes the movable joints, especially the shoulder and elbow during treatment.

In U.S. Pat. No. 4,349,016 issued Sept. 14, 1982, Glassman, Kia and Ryling disclose and teach a livestock splint for an animal brace having a shell member. A frame padding is connected to the inside of the shell and a reinforced back is connected to and traverses the back of the shell member.

In Germ. Pat. No. 219,175 issued Feb. 17, 1910, a bandage for the knee of a horse has a spring loaded protection bandage.

SUMMARY OF THE INVENTION

The cat and dog intravenous restraint splint has an adaptive size splint length and a relatively narrow splint width, and can have a U-shaped width contour sized to retain a typical small animal foreleg in the splint contour. An IV catheter is typically inserted in a small animal foreleg, and the intravenous restraint splint applied to the foreleg in less than 60 seconds. The applied splint prevents the animal from flexing its elbow joint by drawing the leg into its body and possibly shutting off the flow of IV fluid. The basic small animal intravenous restraint splint (SAIR) is a washable, reusable, gas sterilizable, plastic base splint utilizing polypropylene, high density polyethylene, polycarbonate, or the like injection moldable, thermoplastic base. The splint length, splint width, and splint width U-shaped contour has a bend in the splint length adaptively sized for a selected size animal elbow. A horizontal slot is disposed across the splint width adjacent a first splint terminus. A longitudinal slot is disposed next adjacent to the splint horizontal slot, longitudinally centrally disposed the splint longitude. A slidable restraining pin is disposed and secured in the longitudinal slot and the restraining pin is secured to a first animal leg restraint strap. The first strap is disposed normal to splint longitude and can be adaptively moved in the longitudinal slot to adapt to the animal carpus position. A paddle shaped restraint member is disposed adjacent to and integral with the splint length, forming the second splint terminus opposed to the first splint terminus. A second leg restraint strap is also disposed and secured normal to the splint longitude, adjacent the splint U-width and below the paddle member and distantly moved from the longitudinal slot. A restraining hook piece is secured and disposed on the same splint face as the first restraining strap, adjacent the horizontal slot.

Operationally, the animal intravenous restraint splint (SAIR) can be used on either the right or left foreleg. In application, a piece of adhesive tape is applied on the animal foreleg with a first tape end at the animal carpus. The tape is then doubled back so that the other tape end is on the ventral aspect of the carpus. A second tape piece is then spirally wound around the animal foot. The doubled adhesive tape end is placed through the horizontal slot and the animal leg lays properly in the SAIR. The double tape end is pressed against the adjacent hook and fastened to the hook. The first restraint strap is fastened around the animal leg at or above the carpus. The second restraint strap is then fastened around the animal humerus. It may also be necessary to further restrain the animal leg by taping the paddle to the anterior trunk of the animal. The entire dorsal radial and ulnar area of the animal is free and the IV catheter is free of interference. The SAIR is also useful for treating open wounds continuously, or immobilizing an animal elbow.

Included in the objects of this invention are:

To provide an immobilization leg splint for animal treatment.

To provide a quick and simple means for restraining an animal leg during IV cathertization.

To provide a means for treating an open wound of an animal.

To provide an adjustable splint (SAIR) for varying size animals, as adaptively required.

To provide a SAIR which can be washed, sterilized and reused in animal veterinary medicine.

Other objects and advantages of this invention are taught in the following description and claims.

BRIEF DESCRIPTION OF THE DRAWINGS

The description of this invention is to be read in conjunction with the following drawings:

FIG. 1 is an isometric perspective view of the cat and dog small animal restraint splint (SAIR).

FIG. 2A is a more detailed plan view of the first terminus of of the SAIR splint. FIG. 2B is a projective view of the second terminus of the SAIR splint.

FIG. 3A is an elevational perspective and partially sectional view of the taping of an animal foreleg preparatory to securing the foreleg in a SAIR splint. FIG. 3B is an elevational perspective view of the foreleg of FIG. 3A disposed and secured in a SAIR splint.

DESCRIPTION OF THE PREFERRED EMBODIMENT OF THE INVENTION

Figure 4A:
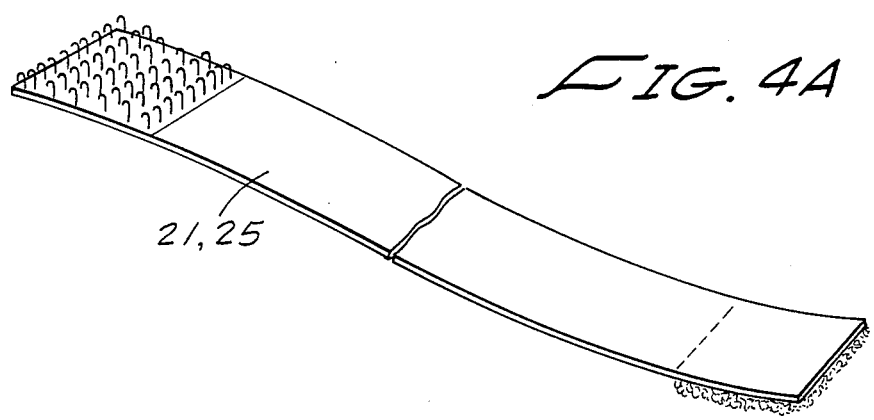
FIG. 4A is a fragmentary plan view of a Velcro strap which can be utilized in securing the animal's leg to the SAIR splint.
Figure 4B:
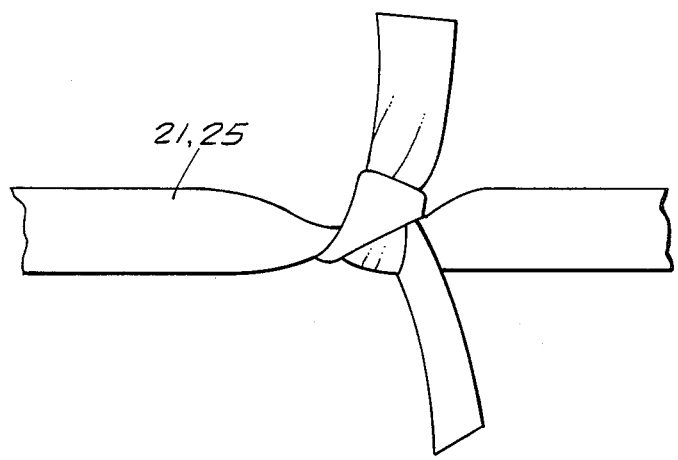
FIG. 4B is a fragmentary projective plan view of a tied strap which can be utilized in securing the animal's leg to the SAIR splint.
Figure 4C:
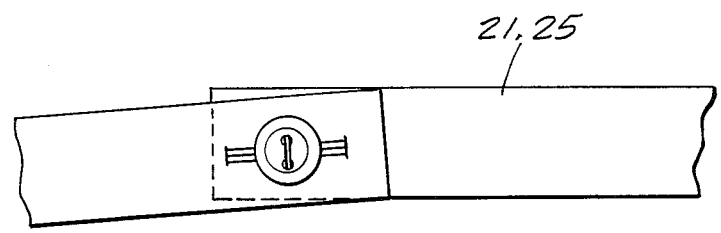
FIG. 4C is a fragmentary plan view of the button securing means which can secure an animal leg to a SAIR splint.
Figure 5:
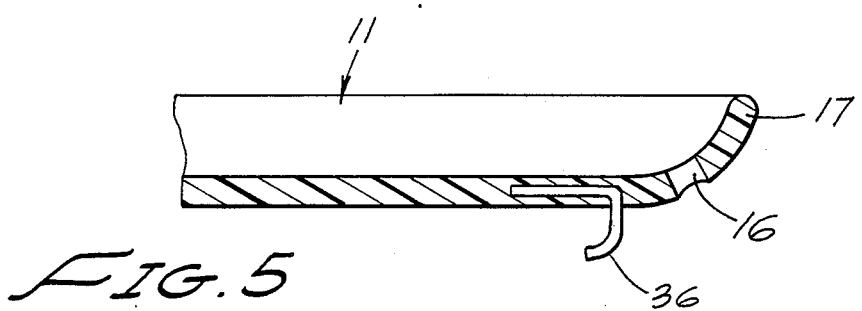
FIG. 5 is a partial sectional view through the SAIR splint illustrating the embodiment of the hook 36 secured in the SAIR splint 10.

Referring to FIG. 1 in detail, the veterinary medical leg splint 10, which is suitable for restraining the cat and dog small animal leg, is shown in perspective view. The leg splint 10 has a longitudinal thermoplastic base splint 11 of selected length 12, width 13, and U-shaped width contour 14. The splint 11 has an upwardly adaptively sized and spaced bend 15 disposed at a position selected for a specific selectively sized animal elbow.

Referring to FIGS. 1 and 2A, a horizontal slot 16 is disposed through and across the splint width 13 adjacent to the splint first terminus 17. A longitudinal slot 18 of selected length 19 is disposed in splint length 12, next to slot 16, selectively spaced in splint 11 next away from slot 16. A restraint pin 20 is slidably permanently secured in the longitudinal slot 18. A restraining strap 21 is permanently disposed on and secured to pin 20, normal to the splint length 12, and having a restraining strap length 22 adaptively sized to the required value for a selected size animal. The U-shaped contour width 14 is clearly shown in FIG. 2A, with a special animal elbow contour at 15.

In FIGS. 1 and 2B there is shown the flat face of paddle 23 disposed normal to the splint width 13, and splint paddle 23 is permanently sized and permanently secured adjacent to the second splint terminus 24. The second restraining flexible strap 25 is also secured and disposed normal to the splint length 12, between the splint paddle 23 and the bend 15 in the splint.

Operatively, the small animal IV catheter is normally first positioned in the animal cephalic vein. See FIG. 3A. Next, a long piece of adhesive is placed on the animal foreleg with one tape end 30 at the animal carpus 31. The tape is then doubled back 32 so that the other tape end is on the ventral aspect 33 of the carpus 31. A second tape piece 34 is then loosely placed around the distal foot of the animal in a spiral wrap and squeezed to the animal foot. The other double tape end 35 of the bandage is placed through the slot 16, and pulled into position, laying the animal's leg properly in the small animal restraint splint. Finally, the tape end 35 is hooked on the metal hook 36, which is disposed in and on the splint 11 on the splint face opposed to the contour 14, restraining the tape end 35 and the animal foreleg movement, as in FIG. 3B. It is important that the restraint be at or above the animal carpus.

The upper splint restraint can be positioned by wrapping a gauze bandage around the paddle 23 and the animal humerus, and taping the bandage in place, stabilizing the splint's rotation.

The above operative procedure leaves the entire radial and ulnar area free for IV administration.

The restraint splint 11 through paddle 23 can be a single injection molded plastic piece, formed and shaped of a sterilizable inexpensive plastic, such as polypropylene, high density polyethylene. The restraining straps 21 and 25 can be sized as required in length and width, and can consist of Velcro fastening straps, cloth tape straps of lengths for tying together, or button securing plastic or rubber tapes or the like. The metal hook 36 is secured in the plastic splint 11, on molding or the like. The small animal restraint splint 10 is sterilizable by steam or ethylene oxide.

The splint 10 can be used on either the animal right or left leg, and can be made in several sizes or lengths for small animals, cats, or large dogs.

Many modifications in the small animal intravenous restraint splint can be made in the light of my teachings. It is understood that within the scope of the claims, the invention can be practiced otherwise than as described.

I claim:
1. A cat and dog restraint combination comprising:
   a longitudinal, thermoplastic splint having a selected length, width, and U-shaped width contour, said splint having a bend in the splint at a length adaptively sized for a selectively sized cat and dog elbow,
   a horizontal slot disposed in and across said splint width adjacent a first splint terminus, said slot of sufficient size to accept a pair securing means which secures the end of an animal leg to the said first splint terminus,
   a longitudinal slot of selected length disposed in and lengthwise in the splint adjacent said horizontal slot and said first splint terminus,
   a restraint pin slidably permanently disposed in said longitudinal slot,
   a first restraining flexible strap secured to said restraining pin, having a selected length and width, said first strap disposed normal to said splint and secured to aforesaid slidable restraint pin,
   a flat paddle having a selected size disposed and terminally secured adjacent a second splint terminus and integral therewith and having a paddle face disposed normal to the width of said splint,
   said paddle aligned with a longitudinal axis of said splint, said paddle adapted to receive a second securing means which secures said paddle to an animal torso, which also immobilizes said splint and leg relative to the animal torso, and,
   a second restraining flexible strap normally secured to said splint, said strap having a selected length and width, said strap disposed on said splint between said paddle and said bend in said splint.

2. In the cat and dog restraint splint of claim 1, the further modification wherein,
   said first restraining strap and said second restraining strap have Velcro securing means disposed thereon, capable of securing cat and dog limbs to said splint.

3. In the cat and dog restraint splint of claim 1, the further modification wherein,
   said first restraining strap and said second restraining strap have strap lengths capable of tying cat and dog limbs to said splint.

4. In the cat and dog restraint splint of claim 1, the further modification wherein,
   said first restraining strap and said second restraining strap each have button securing means disposed thereon, capable of securing cat and dog limbs to said splint.

5. In the cat and dog restraint splint of claim 1 the further modification wherein,
   a hook having a straight base section and a curved section is secured and disposed in said splint by said straight base section adjacent said horizontal slot and on the splint face opposed to said U-shaped contour, said curved hook section having the hook point openly disposed toward said first restraint strap.

* * * * *